United States Patent [19]
Mariani et al.

[11] 4,391,817
[45] Jul. 5, 1983

[54] PYRROLO-DIAZEPINE DERIVATIVES AND THEIR PHARMACEUTICAL COMPOSITIONS

[75] Inventors: Luigi Mariani; Giorgio Tarzia, both of Milan, Italy

[73] Assignee: Gruppo Lepetit S.p.A., Milan, Italy

[21] Appl. No.: 381,271

[22] Filed: May 24, 1982

[30] Foreign Application Priority Data

Jun. 8, 1981 [IT] Italy .............................. 22177 A/81

[51] Int. Cl.³ ..................... A61K 31/55; C07D 487/04
[52] U.S. Cl. .............................. 424/274; 260/239.3 B
[58] Field of Search .................. 260/239.3 B; 424/274

[56] References Cited

U.S. PATENT DOCUMENTS

4,022,766  5/1977  Fontanella et al. ........... 260/239.3 B

FOREIGN PATENT DOCUMENTS

826925  3/1975  Belgium ....................... 260/239.3 B

*Primary Examiner*—Robert T. Bond
*Attorney, Agent, or Firm*—William J. Stein; Gary D. Street; Raymond A. McDonald

[57] ABSTRACT

A new class of pyrrolo-diazepines with anticonvulsant and anti-anxiety activity of the general formula

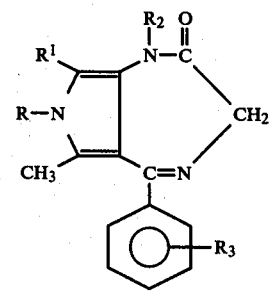

wherein R is $(C_1-C_4)$alkyl, $R_1$ is chloro, bromo or nitro, $R_2$ is hydrogen or $(C_1-C_4)$alkyl and $R_3$ is hydrogen, chloro, bromo, fluoro, trifluoromethyl or methoxy. The new compounds are prepared starting from the corresponding compounds wherein $R_1$ is hydrogen through halogenation or nitration. Pharmaceutical preparations containing the new compounds of formula I are also described.

6 Claims, No Drawings

PYRROLO-DIAZEPINE DERIVATIVES AND THEIR PHARMACEUTICAL COMPOSITIONS

The present invention refers to new pyrrolo[3,4-e][1,4]diazepin-2(1H)-one derivatives of general formula I

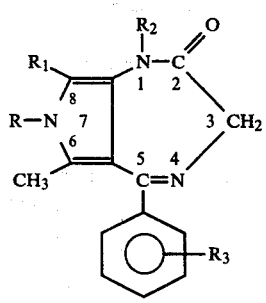

wherein R represents methyl, ethyl, propyl, 1-methylethyl, butyl, 1-methylpropyl, 2-methylpropyl, or 1,1-dimethylethyl, $R_1$ indicates a chlorine or bromine atom or a nitro group, $R_2$ is hydrogen, methyl, ethyl, propyl, 1-methylethyl, butyl, 1-methylpropyl, 2-methylpropyl, or 1,1-dimethylethyl, and $R_3$ is hydrogen, chloro, bromo, fluoro, trifluoromethyl or methoxy.

The new compounds of the present invention are useful as anticonvulsant and antianxiety agents.

A preferred group of compounds comprises those compounds of formula I wherein R is methyl, $R_1$ is chloro, bromo or nitro, $R_2$ is hydrogen or methyl and $R_3$ is hydrogen, chloro or fluoro.

A most preferred group comprises those compounds of formula I wherein R is methyl, $R_1$ is chloro, bromo or nitro, $R_2$ is hydrogen, and $R_3$ is hydrogen or chloro.

The compounds of the present invention are prepared from the corresponding pyrrolo[3,4-e][1,4]diazepin-2(1H)-ones of formula II

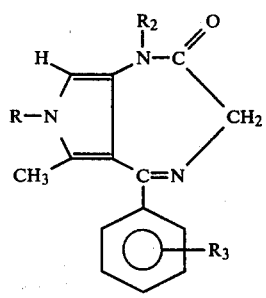

wherein R, $R_2$, and $R_3$ are as defined above, through halogenation or nitration of position 8.

These reactions are easily carried out according to the usual procedures known to any person skilled in the art. In particular these reactions are carried out at low temperature, preferably comprising between −65° C. and −40° C., and in the presence of an organic solvent which does not interfere with the course of the reaction, such as for instance methylene chloride, chloroform, ethyl ether, carbon disulfide, methyl alcohol and the like, using a suitable halogenating or nitrating agent.

As for the chlorination, the reaction proceeds with optimum yields using sulphuryl chloride as the chlorinating agent, however, other different chlorinating agents can be employed such as N-chlorosuccinimide, chlorine, and phosphorous pentachloride; analogously for the bromination, while according to the usual methods bromine is preferred, other agents, such as N-bromosuccinimide, may advantageously be employed. As for the nitration, a nitronium salt such as nitronium fluoborate or nitronium trifluoromethansulfonate, is a particularly effective nitrating agent.

The reaction is complete in a rather short period of time, generally ranging between 15 minutes and 3–4 hours, and the desired product which forms is then recovered by means of conventional techniques which comprise dilution of the reaction mixture with water, treatment with bases to neutralize the acid which formed during the reaction and recovery of the product from the organic phase. The starting compounds of formula II and their preparation are described in Belgian Pat. No. 826,925.

The novel compounds of the present invention possess anticonvulsant and anti-anxiety activity.

To evaluate the anticonvulsant activity, the compounds of the present invention have been submitted to the antipentylenetetrazole bioassay in mice. The experiments have been carried out by following essentially the methodology described by Berger in J. Pharm. Exptl. Ther. 104, 468, (1952). More particularly, a fatal dose of pentylenetetrazole (140 mg/kg s.c.) was administered to groups of ten mice each, treated, 30 minutes before the administration of the convulsant agent, with a selected dose of the potential anticonvulsant compound. One of these groups, the "control group", did not receive the anticonvulsant but only the convulsant agent. Since the animals of the control group died within 30 minutes, the effectiveness of the compounds tested, at each dose tested, was expressed as the number of animals of the group which were still alive two hours after the administration of pentylenetetrazole, out of the total number of animals of the group (10).

The results obtained in these experiments are reported in the following Table:

TABLE

| Compound of example No. | Dose (mg/kg p.o.) | Protected/treated |
| --- | --- | --- |
| 1 | 25 | 7/10 |
| 2 | 15 | 6/10 |
| 3 | 100 | 8/10 |

The compounds of the present invention showed also a remarkable antianxiety activity as confirmed by behavioural tests in mice carried out by following the methodology described by S. Irwin in Psychopharmacologia (Berl.), 13, 222–57, (1968).

These favorable pharmacological properties of the compounds of the present invention are accompanied by a low toxicity. The $LD_{50}$s of the compounds of the present invention, i.e. the doses lethal in 50% of the treated animals, in mice, following intraperitoneal administration, are in fact always higher than 600 mg/kg.

In view of the above, the use of the compounds of the present invention as anticonvulsant and anti-anxiety agents is a further specific object of the present invention.

With the term "use" it is intended to refer to all industrially applicable aspects and acts of said use, including the embodiment of the novel compounds into pharmaceutical compositions.

Suitable pharmaceutical compositions contain the novel compounds in admixture or conjunction with organic or inorganic, solid or liquid pharmaceutical excipients and may be employed for enteral and parenteral administration. Suitable excipients are substances that do not react with the new compounds such as for instance, water, gelatin, lactose, starches, magnesium stearate, talcum, vegetable oils, benzyl alcohol, polyalkyleneglycols, or other known medicinal excipients. The new compounds may be administered by various routes: orally, intramuscularly or intraveneously, for example. For oral administration the substances are compounded in such forms as tablets, dispersible powders, capsules, granules, syrups, elixirs and solutions. For intravenous or intramuscular administration the active ingredients are embodied into injectable dosage forms. Such compositions are formulated as known in the art.

The dosage regimen for the compounds of the present invention in accord with anticonvulsant, antianxiety treatment will depend upon a variety of factors including the particular compound used, the route of administration, and the type of treatment applied for. Good results can be obtained however by administering the compounds of the present invention at a daily dosage range comprising between about 0.05 and about 3 mg/kg preferably in divided doses. It is however clear that a daily dosage beyond the above indicated range may also be employed depending on the individual conditions of the subject to be treated. Accordingly, the present invention provides a therapeutic composition containing from about 2.5 to about 150 mg of one of the compounds of the invention as the active ingredient together with a pharmaceutically acceptable carrier. Following are illustrative pharmaceutical formulations which may be employed in practicing the present invention.

| Preparation of a tablet formulation | Per tablet |
| --- | --- |
| 8-chloro-3,7-dihydro-6,7-dimethyl-5-phenyl-pyrrolo[3,4-e][1,4]diazepin-2(1H)-one | 80 mg |
| starch | 80 mg |
| Aerosil ® V200 | 1.5 mg |
| Magnesium stearate | 1 mg |
| lactose | q.s. to 250 mg |

| Preparation of a capsule formulation | Per capsule |
| --- | --- |
| 8-bromo-3,7-dihydro-6,7-dimethyl-5-phenyl-pyrrolo[3,4-e][1,4]diazepin-2(1H)-one | 100 mg |
| starch | 100 mg |
| Magnesium stearate | 1.5 mg |
| lactose | q.s. to 300 mg |

The following examples describe in details some of the compounds of the present invention and the process for preparing them, but they are not to be considered as a limitation to the scope of the invention:

EXAMPLE 1

8-bromo-3,7-dihydro-6,7-dimethyl-5-phenylpyrrolo[3,4-e][1,4]diazepin-2(1H)-one 3,7-dihydro-6,7-dimethyl-5-phenylpyrrolo[3,4-e][1,4]diazepin-2(1H)-one (5.0 g, 0.020 mole) is dissolved in methanol (150 ml) and the obtained solution is cooled to $-60°$ C. and stirred during the addition of a solution of bromine (3.4 g, 0.021 mole) in methanol (10 ml). After 20 minutes at $-60°$ C., the reaction mixture is poured into an aqueous solution of NaHCO$_3$ (1.5% w/v, 750 ml). The precipitate which forms is recovered by filtration and crystallized from methanol yielding 4.2 g of the compound of the title. M.p. 200°-2° C.

| Elemental analysis: | % C | % H | % N |
| --- | --- | --- | --- |
| Calculated for C$_{15}$H$_{14}$BrN$_3$O | 54.23 | 4.24 | 12.64 |
| found | 54.30 | 4.26 | 12.22 |

EXAMPLE 2

8-chloro-3,7-dihydro-6,7-dimethyl-5-phenylpyrrolo[3,4-e][1,4]diazepin-2(1H)-one

A solution of freshly distilled sulphuryl chloride (4.0 ml) in methylene chloride (40 ml) is added dropwise over a period of 20 minutes to a solution of 3,7-dihydro-6,7-dimethyl-5-phenylpyrrolo[3,4-e][1,4]diazepin-2(1H)-one (5.0 g) in methylene chloride (80 ml) cooled to $-60°$ C. and maintained under inert atmosphere. The reaction is allowed to proceed at $-55°$ C.$\pm 5°$ C. for one hour, then the reaction mixture is poured into a 5% aqueous solution of NaHCO$_3$ (210 ml) and vigorously stirred for 20 minutes. The organic phase is separated, washed with water, dried and evaporated to dryness under vacuum. The obtained residue is crystallized from ethanol yielding 3.7 g of the compound of the title. M.p. 195° C. with decomposition.

| Elemental analysis | % C | % H | % N |
| --- | --- | --- | --- |
| Calculated for C$_{15}$H$_{14}$ClN$_3$O | 62.61 | 4.90 | 14.60 |
| Found | 62.53 | 4.92 | 14.49 |

EXAMPLE 3

3,7-dihydro-6,7-dimethyl-8-nitro-5-phenylpyrrolo[3,4-e][1,4]diazepin-2(1H)-one

Nitric acid (6.0 g, 1.51 g/ml) is added at room temperature to a solution of trifluoromethanesulfonic acid (24 g) in methylene chloride (400 ml) kept under an inert atmosphere. The reaction mixture is stirred at room temperature for 10 minutes and then cooled to $-60°$ C.

3,7-dihydro-6,7-dimethyl-5-phenylpyrrolo[3,4-e][1,4]diazepin-2(1H)-one (5 g) is added quickly to the obtained suspension of nitronium trifluoromethanesulfonate and the reaction is allowed to proceed at $-60°$ C. for 3 hours. The reaction mixture is then poured onto crushed ice (400 g) and stirred till the temperature reaches 15°-20° C. The residue is collected by filtration, triturated with 10% aqueous NaOH and extracted with methylene chloride. The organic layer is washed with water, dried and evaporated under *vacuum* and the obtained residue is crystallized from methanol yielding 1.3 g of the title compound. M.p. 232°-34° C.

| Elemental analysis: | % C | % H | % N |
| --- | --- | --- | --- |
| Calculated for C$_{15}$H$_{14}$N$_4$O$_3$ | 60.39 | 4.73 | 18.78 |
| Found | 60.58 | 4.73 | 18.90 |

We claim:

1. A pyrrolo[3,4-e][1,4]diazepin-2(1H)-one of the formula

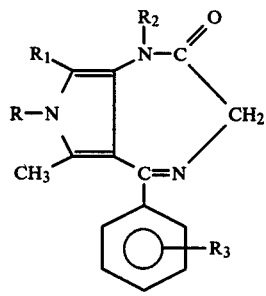

wherein R represents methyl, ethyl, propyl, 1-methylethyl, butyl, 1-methylpropyl, 2-methylpropyl, or 1,1-dimethylethyl, $R_1$ designates a chlorine or bromine atom or a nitro group, $R_2$ represents hydrogen, methyl, ethyl, propyl, 1-methylethyl, butyl, 1-methylpropyl, 2-methylpropyl, or 1,1-dimethylethyl, and $R_3$ is hydrogen, chloro, bromo, fluoro, trifluoromethyl or methoxy.

2. A compound according to claim 1 wherein R is methyl, $R_1$ is chloro, bromo or nitro, $R_2$ is hydrogen or methyl and $R_3$ is hydrogen, chloro or fluoro.

3. A compound according to claim 1 wherein R is methyl, $R_1$ is chloro, bromo or nitro, $R_2$ is hydrogen and $R_3$ is hydrogen or chloro.

4. A process for preparing a compound of formula

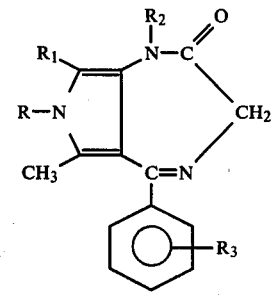

wherein R represents methyl, ethyl, propyl, 1-methylethyl, butyl, 1-methylpropyl, 2-methylpropyl, or 1,1-dimethylethyl, $R_1$ designates a chlorine or bromine atom or a nitro group, $R_2$ represents hydrogen, methyl, ethyl, propyl, 1-methylethyl, butyl, 1-methylpropyl, 2-methylpropyl, or 1,1-dimethylethyl, and $R_3$ is hydrogen, chloro, bromo, fluoro, trifluoromethyl or methoxy, which comprises nitrating or halogenating a compound of formula II

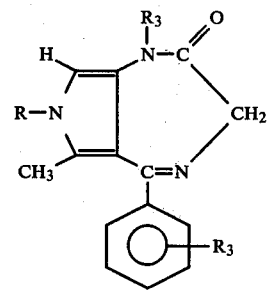

wherein R, $R_2$ and $R_3$ are as defined above.

5. An anticonvulsant and antianxiety pharmaceutical preparation containing an effective amount of a compound of claim 1 as the active ingredient, along with a suitable pharmaceutical carrier.

6. A pharmaceutical preparation according to claim 5 which contains from 2.5 to about 150 mg of active ingredient per unit dosage form.

* * * * *